(12) United States Patent
Ali et al.

(10) Patent No.: US 7,858,325 B2
(45) Date of Patent: *Dec. 28, 2010

(54) METHOD OF DIAGNOSING, MONITORING, STAGING, IMAGING AND TREATING PROSTATE CANCER

(75) Inventors: Shujath Ali, Newtown, CA (US); Yongming Sun, Redwood City, CA (US); Susana Salceda, San Jose, CA (US); Herve Recipon, San Francisco, CA (US); Robert Cafferkey, Sunnyvale, CA (US)

(73) Assignee: Diadexus, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/043,184

(22) Filed: Mar. 6, 2008

(65) Prior Publication Data

US 2008/0175788 A1 Jul. 24, 2008

Related U.S. Application Data

(60) Continuation of application No. 10/929,973, filed on Aug. 30, 2004, now Pat. No. 7,364,862, which is a division of application No. 09/807,200, filed as application No. PCT/US99/23764 on Oct. 18, 1999, now Pat. No. 6,960,433.

(60) Provisional application No. 60/104,741, filed on Oct. 19, 1998.

(51) Int. Cl.
*G01N 33/53* (2006.01)
(52) U.S. Cl. ........................ 435/7.1; 530/350
(58) Field of Classification Search ............ 435/7.1; 530/350
See application file for complete search history.

(56) References Cited

U.S. PATENT DOCUMENTS

| 5,871,969 | A | 2/1999 | Hastings et al. |
| 7,364,862 | B2 * | 4/2008 | Ali et al. ............ 435/7.1 |

FOREIGN PATENT DOCUMENTS

| EP | 1130094 A2 | 9/2001 |
| WO | WO 97/29189 A1 | 8/1997 |
| WO | WO 98/45442 | 10/1998 |
| WO | WO 98/45442 A2 | 10/1998 |
| WO | WO 98/50073 A1 | 11/1998 |
| WO | WO 99/46281 A2 | 9/1999 |
| WO | WO 99/58642 A2 | 11/1999 |
| WO | WO 00/23108 A1 | 4/2000 |
| WO | WO 00/23111 A1 | 4/2000 |
| WO | WO 00/37638 A2 | 6/2000 |
| WO | WO 00/53756 A2 | 9/2000 |
| WO | WO 00/53758 A2 | 9/2000 |
| WO | WO 00/55199 A1 | 9/2000 |
| WO | WO 00/55375 A1 | 9/2000 |
| WO | WO 01/22920 A2 | 4/2001 |
| WO | WO 01/44291 A2 | 6/2001 |
| WO | WO 01/53312 A1 | 7/2001 |

OTHER PUBLICATIONS

Schmid S et al, 2001 (J comparative Neurology, 430(2): 160-71).*
Conner et al, 1996 (Mol Brain Res, 42: 1-17).*
MPSRCH search result, 2009, us-12-043184.2.rapbn, result 1, p. 1.*
Hell et al, 1995 (Laboratory Investigation, vol. 73, pp. 492-496).
Guo et al, 2002 (Journal of Pharmacology and Experimental Therapeutics, vol. 300, pp. 206-212).
Schmid S et al, 2001 (J comparative Neurology, 430(2): 160-71).
Conner et al, 1996 (Mol Brain Res, 42: 1-17).
Greenbaum et al. (Genome Biology, 2003, vol. 4, Issue 9, pp. 117.1-117.8).
Fu et at 1996 (EMBO Journal, vol. 15, pp. 4392-4401).
Yokota, J et al, 1988 (Oncogene, vol. 3, pp. 471-475).
Zimmer, 1991 (Cell Motility and the Cytoskeleton, vol. 20, pp. 325-337).
Kibel, As et al, 2000, J urol, 164(1); 192-6.
Zhau, He, 1994, J Cell Biochem, Suppl 19: 208-216.
Ren, C et al, 1998, Cancer Res, 58(6): 1285-90.
Gingrich, Jr. et al, 1996, Cancer res, 56(18): 4096-4102.
Russo, V et al, 1995, Int J Cancer, 64: 216-221.
MPSRCH search report, 2007, us-10-929973.2.rag, result 3, pp. 1-2.
Dong et al, 2000, Cancer Research, 60: 3380-3883.
Burstyn-Cohen et al. F-Spondin is Required for Accurate Pathfinding of Commissural Axons at the Floor Plate, Neuron, 1999, vol. 23, pp. 233-246.
Higashijima et al. Mindin/F-spondin Family: Novel ECM Proteins Expressed in the Zebrafish Embryonic Axis, Developmental Biology, 1997, vol. 192, pp. 211-227.
Manda et al. Identification of Genes (SPON2 and C20orf2) Differentially Expressed between Cancerous and Noncancerous Lung Cells by mRNA Differential Display, Genomics, 1999, vol. 61, pp. 5-14.
Umemiya et al. M-Spondin, a Novel ECM Protein Highly Homologous to Vertebrate F-Spondin, is Localized at the Muscle Attachment Sites in the *Drosophila* Embryo, Developmental Biology, 1997, vol. 186, pp. 165-176.

* cited by examiner

*Primary Examiner*—Misook Yu
*Assistant Examiner*—Minh-Tam Davis
(74) *Attorney, Agent, or Firm*—Licata & Tyrrell P.C.; Keith R. McCollum

(57) ABSTRACT

The present invention provides a new method for detecting, diagnosing, monitoring, staging, prognosticating, imaging and treating prostate cancer.

3 Claims, No Drawings

SEQUENCE LISTING

<160> NUMBER OF SEQ ID NOS: 5

<210> SEQ ID NO 1
<211> LENGTH: 1840
<212> TYPE: DNA
<213> ORGANISM: Homo sapien

```
<400> SEQUENCE: 1
ctcgagccgg ggtgcggcag cactgccagg ggaagagggt gatccgaccc ggggaaggtc      60
gctgggcagg gcgagttggg aaagcggcag ccccgccgc ccccgcagcc ccttctcctc      120
cttctcccca cgtcctatct gcctctcgct ggaggccagg ccgtgcagca tcgaagacag     180
gaggaactgg agcctcattg gccggcccgg ggcgccggcc tcgggcttaa ataggagctc     240
cgggctctgg ctgggacccg accgctgccg gccgcgctcc cgctgctcct gccgggtgat     300
ggaaaacccc agcccggccg ccgccctggg caaggccctc tgcgctctcc tcctggccac     360
tctcggcgcc gccggccagc tcttggggg agagtccatc tgttccgcca gagccccggc      420
caaatacagc atcaccttca cgggcaagtg gagccagacg gccttcccca agcagtaccc     480
cctgttccgc ccccctgcgc agtggtcttc gctgctgggg gccgcgcata gctccgacta     540
cagcatgtgg aggaagaacc agtacgtcag taacgggctg cgcgactttg cggagcgcgg     600
cgaggcctgg gcgctgatga aggagatcga ggcggcgggg gaggcgctgc agagcgtgca     660
cgaggtgttt tcggcgcccg ccgtccccag cggcaccggg cagacgtcgg cggagctgga     720
ggtgcagcgc aggcactcgc tggtctcgtt tgtggtgcgc atcgtgccca gccccgactg     780
gttcgtgggc gtggacagcc tggacctgtg cgacggggac cgttggcggg aacaggcggc     840
gctggacctg tacccctacg acgccgggac ggacagcggc ttcaccttct cctcccccaa     900
cttcgccacc atcccgcagg acacggtgac cgagataacg tcctcctctc ccagccaccc     960
ggccaactcc ttctactacc cgcggctgaa ggccctgcct cccatcgcca gggtgacact    1020
ggtgcggctg cgacagagcc ccagggcctt catccctccc gccccagtcc tgcccagcag    1080
ggacaatgag attgtagaca cgcctcagt tccagaaacg ccgctggact gcgaggtctc     1140
cctgtggtcg tcctggggac tgtgcggagg ccactgtggg aggctcggga ccaagagcag    1200
gactcgctac gtccgggtcc agcccgccaa caacgggagc ccctgccccg agctcgaaga    1260
agaggctgag tgcgtccctg ataactgcgt ctaagaccag agcccgcag cccctggggc     1320 cccccggagc catggggtgt cggggctcc tgtgcaggct catgctgcag gcggccgagg    1380 gcacagggg tttcgcgctg ctcctgaccg cggtgaggcc gcgccgacca tctctgcact    1440
gaagggccct ctggtggccg gcacgggcat tgggaaacag cctcctcctt tcccaacctt   1500
gcttcttagg ggcccccgtg tccgtctgc tctcagcctc ctcctcctgc aggataaagt    1560
catccccaag gctccagcta ctctaaatta tgtctcctta taagttattg ctgctccagg    1620
agattgtcct tcatcgtcca ggggcctggc tcccacgtgt tgcagatac ctcagacctg    1680 gtgctctagg ctgtgctgag cccactctcc cgagggcgca tccaagcggg ggccacttga    1740
gaagtgaata aatggggcgg tttcggaagc gtcagtgttt ccatgttatg gatctctctg   1800
cgtttgaata aagactatct ctgttgctca aaaaaaaaa                           1840

<210> SEQ ID NO 2
<211> LENGTH: 331
<212> TYPE: PRT
<213> ORGANISM: Homo sapien

<400> SEQUENCE: 2

Met Glu Asn Pro Ser Pro Ala Ala Ala Leu Gly Lys Ala Leu Cys Ala
1               5                   10                  15

Leu Leu Leu Ala Thr Leu Gly Ala Ala Gly Gln Pro Leu Gly Gly Glu
            20                  25                  30

Ser Ile Cys Ser Ala Arg Ala Pro Ala Lys Tyr Ser Ile Thr Phe Thr
```

-continued

```
              35                  40                  45
Gly Lys Trp Ser Gln Thr Ala Phe Pro Lys Gln Tyr Pro Leu Phe Arg
 50                  55                  60

Pro Pro Ala Gln Trp Ser Ser Leu Leu Gly Ala Ala His Ser Ser Asp
 65                  70                  75                  80

Tyr Ser Met Trp Arg Lys Asn Gln Tyr Val Ser Asn Gly Leu Arg Asp
                 85                  90                  95

Phe Ala Glu Arg Gly Glu Ala Trp Ala Leu Met Lys Glu Ile Glu Ala
            100                 105                 110

Ala Gly Glu Ala Leu Gln Ser Val His Glu Val Phe Ser Ala Pro Ala
        115                 120                 125

Val Pro Ser Gly Thr Gly Gln Thr Ser Ala Glu Leu Glu Val Gln Arg
130                 135                 140

Arg His Ser Leu Val Ser Phe Val Val Arg Ile Val Pro Ser Pro Asp
145                 150                 155                 160

Trp Phe Val Gly Val Asp Ser Leu Asp Leu Cys Asp Gly Asp Arg Trp
                165                 170                 175

Arg Glu Gln Ala Ala Leu Asp Leu Tyr Pro Tyr Asp Ala Gly Thr Asp
            180                 185                 190

Ser Gly Phe Thr Phe Ser Ser Pro Asn Phe Ala Thr Ile Pro Gln Asp
        195                 200                 205

Thr Val Thr Glu Ile Thr Ser Ser Pro Ser His Pro Ala Asn Ser
210                 215                 220

Phe Tyr Tyr Pro Arg Leu Lys Ala Leu Pro Pro Ile Ala Arg Val Thr
225                 230                 235                 240

Leu Val Arg Leu Arg Gln Ser Pro Arg Ala Phe Ile Pro Pro Ala Pro
                245                 250                 255

Val Leu Pro Ser Arg Asp Asn Glu Ile Val Asp Ser Ala Ser Val Pro
            260                 265                 270

Glu Thr Pro Leu Asp Cys Glu Val Ser Leu Trp Ser Trp Gly Leu
        275                 280                 285

Cys Gly Gly His Cys Gly Arg Leu Gly Thr Lys Ser Arg Thr Arg Tyr
290                 295                 300

Val Arg Val Gln Pro Ala Asn Asn Gly Ser Pro Cys Pro Glu Leu Glu
305                 310                 315                 320

Glu Glu Ala Glu Cys Val Pro Asp Asn Cys Val
                325                 330

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
gccttcagcc gtgggtagt                                                  19

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gacagcggct tcaccttctc                                                 20
```

<210> SEQ ID NO 5
<211> LENGTH: 1006
<212> TYPE: DNA
<213> ORGANISM: Homo sapien
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (976)..(976)
<223> OTHER INFORMATION: n is a, c, g, or t
<220> FEATURE:
<221> NAME/KEY: misc_feature
<222> LOCATION: (978)..(979)
<223> OTHER INFORMATION: n is a, c, g, or t
<220> FEATURE:
<221> NAME/KEY: misc_feature
<222> LOCATION: (983)..(985)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (989)..(989)
<223> OTHER INFORMATION: n is a, c, g, or t
<220> FEATURE:
<221> NAME/KEY: misc_feature
<222> LOCATION: (992)..(992)
<223> OTHER INFORMATION: n is a, c, g, or t
<220> FEATURE:
<221> NAME/KEY: misc_feature
<222> LOCATION: (1000)..(1000)
<223> OTHER INFORMATION: n is a, c, g, or t

<400> SEQUENCE: 5

```
gacagcggct tcaccttctc ctcccccaac ttcgccacca tcccgcagga cacggtgacc      60
gagataacgt cctcctctcc cagccacccg gccaactcct tctactaccc acggctgaag     120
gccctgcctc ccatcgccag ggtgacactg ctgcggctgc dacagagccc ccagggcctt     180
catccctccc gccccagtcc tgcccagcag ggacaatgag attgtagaca gcgcctcagt     240
tccagaaacg ccgctggact gcgaggtctc cctgtggtcg tcctggggac tgtgcggagg     300
ccactgtggg aggctcggga ccaagagcag gactcgctac gtccgggtcc agcccgccaa     360
caacgggagc cctgccccg agctcgaaga agaggctgag tgcgtccctg ataactgcgt     420
ctaagaccag agccccgcag ccctggggc ccccggagc catgggtgt cgggggctcc        480 tgtgcaggct catgctgcag gcggccgagg gcacaggggg tttcgcgctg ctcctgaccg     540
cggtgaggcc gcgccgacca tctctgcact gaagggccct ctggtggccg gcacgggcat     600
tgggaaacag cctcctcctt tcccaacctt gcttcttagg ggccccgtg tccgtctgc      660 tctcagcctc ctcctcctgc aggataaagt catcccaag gctccagcta ctctaaatta     720
tgtctcctta taagttattg ctgctccagg agattgtcct tcatcgtcca ggggcctggc    780
tcccacgtgg ttgcagatac ctcagacctg gtgctctagg ctgtgctgag cccactctcc    840
cgagggcgca tccaagcggg ggccacttga gaagtgaata aatggggcgg tttcggaagc    900
gtcagtgttt ccatgttatg gatctctctg cgtttgaata aagactatct ctgttgctca    960 caaaaaaaa anatananna aannnanana anccaaattn atcaaa                   1006
```

METHOD OF DIAGNOSING, MONITORING, STAGING, IMAGING AND TREATING PROSTATE CANCER

INTRODUCTION

This application is a continuation of U.S. application Ser. No. 10/929,973 filed Aug. 30, 2004, now patented, U.S. Pat. No. 7,364,862, which is a Divisional of U.S. application Ser. No. 09/807,200 filed May 29, 2001, now patented, U.S. Pat. No. 6,960,433, which is a U.S. National Phase of PCT/US99/23764 filed Oct. 19, 1999, which claims the benefit of U.S. Provisional 60/104,741 filed Oct. 19, 1998, each of which are herein incorporated by reference in their entireties.

FIELD OF THE INVENTION

This invention relates, in part, to newly developed assays for detecting, diagnosing, monitoring, staging, prognosticating, imaging and treating cancers, particularly prostate cancer.

BACKGROUND OF THE INVENTION

Cancer of the prostate is the most prevalent malignancy in adult males, excluding skin cancer, and is an increasingly prevalent health problem in the United States. In 1996, it was estimated that 41,400 deaths would result from this disease in the United States alone, indicating that prostate cancer is second only to lung cancer as the most common cause of death in the same population. If diagnosed and treated early, when the cancer is still confined to the prostate, the chances of cure is significantly higher.

Treatment decisions for an individual are linked to the stage of prostate cancer present in that individual. A common classification of the spread of prostate cancer was developed by the American Urological Association (AUA). The AUA system divides prostate tumors into four stages, A to D. Stage A, microscopic cancer within prostate, is further subdivided into sub-stages A1 and A2. Sub-stage A1 is a well-differentiated cancer confined to one site within the prostate. Treatment is generally observation, radical prostatectomy, or radiation. Sub-stage A2 is a moderately to poorly differentiated cancer at multiple sites within the prostate. Treatment is radical prostatectomy or radiation. Stage B, palpable lump within the prostate, is also further subdivided into sub-stages B1 and B2. In sub-stage B1, the cancer forms a small nodule in one lobe of the prostate. In sub-stage B2, the cancer forms large or multiple nodules, or occurs in both lobes of the prostate. Treatment for sub-stages B1 and B2 is either radical prostatectomy or radiation. Stage C is a large cancer mass involving most or all of the prostate and is also further subdivided into two stages. In sub-stage C1, the cancer forms a continuous mass that may have extended beyond the prostate. In sub-stage C2, the cancer forms a continuous mass that invades the surrounding tissue. Treatment for both these sub-stages is radiation with or without drugs to address the cancer. The fourth stage, Stage D is metastatic cancer and is also subdivided into two sub-stages. In sub-stage D1, the cancer appears in the lymph nodes of the pelvis. In sub-stage D2, the cancer involves tissues beyond lymph nodes. Treatment for both of these sub-stages is systemic drugs to address the cancer as well as pain.

However, current prostate cancer staging methods are limited. As many as 50% of prostate cancers initially staged as A2, B, or C are actually stage D, metastatic. Discovery of metastasis is significant because patients with metastatic cancers have a poorer prognosis and require significantly different therapy than those with localized cancers. The five year survival rates for patients with localized and metastatic prostate cancers are 93% and 29%, respectively.

Accordingly, there is a great need for increasingly sensitive methods for diagnosing and staging of prostate cancer in a human patient to determine whether or not such cancer has metastasized and for monitoring the progress of a cancer which has not metastasized for the onset of metastasis.

In the present invention, methods are provided for detecting, diagnosing, monitoring, staging, prognosticating, imaging and treating prostate cancer via the cancer specific gene referred to herein as CSG. CSG refers, among other things, to native protein expressed by the gene comprising the polynucleotide sequence of SEQ ID NO:1. The amino acid sequence of a polypeptide encoded by SEQ ID NO:1 is depicted herein as SEQ ID NO:2. In the alternative, what is meant by CSG as used herein, means the native mRNA encoded by the gene comprising the polynucleotide sequence of SEQ ID NO:1 or levels of the gene comprising the polynucleotide sequence of SEQ ID NO:1.

Other objects, features, advantages and aspects of the present invention will become apparent to those of skill in the art from the following description. It should be understood, however, that the following description and the specific examples, while indicating preferred embodiments of the invention are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of prostate cancer by analyzing for changes in levels of CSG in cells, tissues or bodily fluids compared with levels of CSG in preferably the same cells, tissues, or bodily fluid type of a normal human control, wherein a change in levels of CSG in the patient versus the normal human control is associated with prostate cancer.

Further provided is a method of diagnosing metastatic prostate cancer in a patient having prostate cancer which is not known to have metastasized by identifying a human patient suspected of having prostate cancer that has metastasized; analyzing a sample of cells, tissues, or bodily fluid from such patient for CSG; comparing the CSG levels in such cells, tissues, or bodily fluid with levels of CSG in preferably the same cells, tissues, or bodily fluid type of a normal human control, wherein an increase in CSG levels in the patient versus the normal human control is associated with prostate cancer which has metastasized.

Also provided by the invention is a method of staging prostate cancer in a human which has such cancer by identifying a human patient having such cancer; analyzing a sample of cells, tissues, or bodily fluid from such patient for CSG; comparing CSG levels in such cells, tissues, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided is a method of monitoring prostate cancer in a human having such cancer for the onset of metastasis. The method comprises identifying a human patient having such cancer that is not known to have metastasized; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which has metastasized.

Further provided is a method of monitoring the change in stage of prostate cancer in a human having such cancer by looking at levels of CSG in a human having such cancer. The method comprises identifying a human patient having such cancer; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided are antibodies targeted against CSG or fragments of such antibodies which can be used to detect or image localization of CSG in a patient for the purpose of detecting or diagnosing a disease or condition. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. These antibodies or fragments thereof can also be used as therapeutic agents in the treatment of diseases characterized by expression of CSG. In therapeutic applications, the antibody can be used without or with derivatization to a cytotoxic agent such as a radioisotope, enzyme, toxin, drug or a prodrug.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

The present invention relates to diagnostic assays and methods, both quantitative and qualitative for detecting, diagnosing, monitoring, staging and prognosticating cancers by comparing levels of CSG in a human patient with those of CSG in a normal human control. What is meant by levels of CSG as used herein, means levels of the native protein expressed by the gene comprising the polynucleotide sequence of SEQ ID NO:1. The amino acid sequence of a polypeptide encoded by SEQ ID NO:1 is depicted herein as SEQ ID NO:2. The native protein being detected, may be whole, a breakdown product, a complex of molecules or chemically modified. In the alternative, what is meant by levels of CSG as used herein, means levels of the native mRNA encoded by the gene comprising the polynucleotide sequence of SEQ ID NO:1 or levels of DNA comprising the polynucleotide sequence of SEQ ID NO:1. Such levels are preferably measured in at least one of cells, tissues and/or bodily fluids, including determination of normal and abnormal levels. Thus, for instance, a diagnostic assay in accordance with the invention for diagnosing over-expression of CSG protein compared to normal control bodily fluids, cells, or tissue samples may be used to diagnose the presence of prostate cancer.

All the methods of the present invention may optionally include measuring the levels of other cancer markers as well as CSG. Other cancer markers, in addition to CSG, useful in the present invention will depend on the cancer being tested and are known to those of skill in the art.

Diagnostic Assays

The present invention provides methods for diagnosing the presence of prostate cancer by analyzing for changes in levels of CSG in cells, tissues or bodily fluids compared with levels of CSG in cells, tissues or bodily fluids of preferably the same type from a normal human control, wherein an increase in levels of CSG in the patient versus the normal human control is associated with the presence of prostate cancer.

Without limiting the instant invention, typically, for a quantitative diagnostic assay a positive result indicating the patient being tested has cancer is one in which cells, tissues or bodily fluid levels of the cancer marker, such as CSG, are at least two times higher, and most preferably are at least five times higher, than in preferably the same cells, tissues or bodily fluid of a normal human control.

The present invention also provides a method of diagnosing metastatic prostate cancer in a patient having prostate cancer which has not yet metastasized for the onset of metastasis. In the method of the present invention, a human cancer patient suspected of having prostate cancer which may have metastasized (but which was not previously known to have metastasized) is identified. This is accomplished by a variety of means known to those of skill in the art.

In the present invention, determining the presence of CSG levels in cells, tissues or bodily fluid, is particularly useful for discriminating between prostate cancer which has not metastasized and prostate cancer which has metastasized. Existing techniques have difficulty discriminating between prostate cancer which has metastasized and prostate cancer which has not metastasized. However, proper treatment selection is often dependent upon such knowledge.

In the present invention, the cancer marker levels measured in such cells, tissues or bodily fluid is CSG. Measured levels of CSG are compared with levels of CSG in preferably the same cells, tissue or bodily fluid type of a normal human control. That is, if the cancer marker being observed is just CSG in serum, this level is preferably compared with the level of CSG in serum of a normal human patient. An increase in CSG levels in the patient versus the normal human control is associated with prostate cancer which has metastasized.

Without limiting the instant invention, typically, for a quantitative diagnostic assay a positive result indicating the cancer in the patient being tested or monitored has metastasized is one in which cells, tissues or bodily fluid levels of the cancer marker, such as CSG, are at least two times higher, and most preferably are at least five times higher, than in preferably the same cells, tissues or bodily fluid of a normal patient.

Normal human control as used herein includes a human patient without cancer and/or non cancerous samples from the patient; in the methods for diagnosing or monitoring for metastasis, normal human control may preferably also include samples from a human patient that is determined by reliable methods to have prostate cancer which has not metastasized.

Staging

The invention also provides a method of staging prostate cancer in a human patient. The method comprises identifying a human patient having such cancer and analyzing a sample of cells, tissues or bodily fluid from such human patient for CSG. The measured CSG levels in the patient are then compared with levels of CSG in preferably the same cells, tissues or bodily fluid type of a normal human control, wherein an increase in CSG levels in the human patient versus the normal human control is associated with a cancer which is progressing and a decrease in the levels of CSG (but still increased over true normal levels) is associated with a cancer which is regressing or in remission.

Monitoring

Further provided is a method of monitoring prostate cancer in a human patient having such cancer for the onset of metastasis. The method comprises identifying a human patient having prostate cancer that is not known to have metastasized; periodically analyzing cells, tissues or bodily fluid from such human patient for CSG; comparing the CSG levels in such cells, tissues or bodily fluid with levels of CSG in preferably the same cells, tissues or bodily fluid type of a normal human control, wherein an increase in CSG levels in the human patient versus the normal human control is associated with a cancer which has metastasized. In this method, normal human control samples may also include prior patient samples.

Further provided by this invention is a method of monitoring the change in stage of prostate cancer in a human patient having such cancer. The method comprises identifying a human patient having prostate cancer; periodically analyzing cells, tissues or bodily fluid from such human patient for CSG; comparing the CSG levels in such cells, tissues or bodily fluid with levels of CSG in preferably the same cells, tissues or bodily fluid type of a normal human control, wherein an increase in CSG levels in the human patient versus the normal human control is associated with a cancer which is progressing in stage and a decrease in the levels of CSG is associated with a cancer which is regressing in stage or in remission. In this method, normal human control samples may also include prior patient samples.

Monitoring patients for onset of metastasis is periodic and preferably done on a quarterly basis. However, monitoring may be performed more or less frequently depending on the cancer, the particular patient, and the stage of the cancer.

Assay Techniques

Assay techniques that can be used to determine levels of gene expression (including protein levels), such as CSG of the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Western Blot analyses, ELISA assays and proteomic approaches: two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to CSG, preferably a monoclonal antibody. In addition a reporter antibody generally is prepared which binds specifically to CSG. The reporter antibody is attached to a detectable reagent such as radioactive, fluorescent or enzymatic reagent. For example, detectable agents such as horseradish peroxidase enzyme and alkaline phosphatase are routinely used in these types of assays.

To carry out the ELISA, antibody specific to CSG is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time CSG binds to the specific antibody attached to the polystyrene dish. Unbound sample is washed out with buffer. A reporter antibody specifically directed to CSG and linked to a detectable reagent such as horseradish peroxidase is placed in the dish resulting in binding of the reporter antibody to any monoclonal antibody bound to CSG. Unattached reporter antibody is then washed out. Reagents for detection of peroxidase activity, including a colorimetric substrate are then added to the dish. Immobilized peroxidase linked to CSG antibodies produces a colored reaction product. The amount of color developed in a given time period is proportional to the amount of CSG protein present in the sample. Quantitative results typically are obtained by reference to a standard curve.

A competition assay can also be employed wherein antibodies specific to CSG are attached to a solid support. Labeled CSG and a sample derived from the host are then passed over the solid support. The amount of label detected which is attached to the solid support can be correlated to a quantity of CSG in the sample.

Nucleic acid methods can be used to detect CSG mRNA as a marker for prostate cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e. gridding) can be used to detect the expression of and quantitate the level of expression of that gene. In this approach, a cDNA encoding the CSG gene is fixed to a substrate. The substrate may be of any suitable type including but not limited to glass, nitrocellulose, nylon or plastic. At least a portion of the DNA encoding the CSG gene is attached to the substrate and then incubated with the analyte, which may be RNA or a complementary DNA (cDNA) copy of the RNA isolated from the tissue of interest. Hybridization between the substrate bound DNA and the analyte can be detected and quantitated by several means including, but not limited to, radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins so that smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes or subsequent protein microsequencing can reveal the relative abundance of a given protein and the identity of the proteins in the sample.

The above tests can be carried out on samples derived from a variety of cells, bodily fluids and/or tissue extracts including both homogenates or solubilized tissue obtained from a human patient. Tissue extracts can be obtained from tissue biopsy and autopsy material. Bodily fluids useful in the present invention include blood, urine, saliva or any other bodily secretion or derivative thereof. By blood it is meant to include whole blood, plasma, serum or any derivative of blood.

In Vivo Antibody Use

Antibodies which specifically bind to CSG can also be used in vivo in patients suspected of suffering from prostate cancer. Specifically, antibodies which specifically bind a CSG can be injected into a patient suspected of having prostate cancer for diagnostic and/or therapeutic purposes. The preparation and use of antibodies for in vivo diagnosis is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247-254). In particular, these antibody-chelators have been used in detecting tumors in patients suspected of having recurrent colorectal cancer (Griffin et al. J. Clin. Onc. 1991 9:631-640). Antibodies with paramagnetic ions as labels for use in magnetic resonance imaging have also been described (Lauffer, R. B. Magnetic Resonance in Medicine 1991 22:339-342). Antibodies directed against CSG can be used in a similar manner. Labeled antibodies which specifically bind CSG can be injected into patients suspected of having prostate cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Localization of the label permits determination of the spread of the cancer. The amount of label within an organ or tissue also allows determination of the presence or absence of cancer in that organ or tissue.

For patients diagnosed with prostate cancer, injection of an antibody which specifically binds CSG can also have a therapeutic benefit. The antibody may exert its therapeutic effect alone. Alternatively, the antibody can be conjugated to a cytotoxic agent such as a drug, toxin or radionuclide to enhance its therapeutic effect. Drug monoclonal antibodies have been described in the art for example by Garnett and Baldwin, Cancer Research 1986 46:2407-2412. The use of toxins conjugated to monoclonal antibodies for the therapy of various cancers has also been described by Pastan et al. Cell 1986 47:641-648. Yttrium-90 labeled monoclonal antibodies have been described for maximization of dose delivered to the tumor while limiting toxicity to normal tissues (Goodwin and Meares Cancer Supplement 1997 80:2675-2680). Other cytotoxic radionuclides including, but not limited to Copper-67, Iodine-131 and Rhenium-186 can also be used for labeling of antibodies against CSG.

Antibodies which can be used in these in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

The present invention is further described by the following examples. These examples are provided solely to illustrate the invention by reference to specific embodiments. These exemplifications, while illustrating certain aspects of the invention, do not portray the limitations or circumscribe the scope of the disclosed invention.

EXAMPLES

The examples are carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 1

Suppression Subtractive Hybridization

CLONTECH PCR-SELECT

CLONTECH PCR-SELECT is a PCR based subtractive hybridization method designed to selectively enrich for cDNAs corresponding to mRNAs differentially expressed between two mRNA populations (Diatchenko et al, *Proc. Natl. Acad. Sci. USA*, Vol. 93, pp. 6025-6030, 1996). In this method, differentially expressed mRNAs are enriched based on a selective amplification. cDNA is prepared from the two mRNA populations which are to be compared. These include the Tester population which is a cDNA population in which the differentially expressed messages are sought and the Driver population which is a cDNA population in which the differentially expressed transcripts are absent or low. The tester sample is separated in two parts and different PCR adapters are ligated to the 5' ends. Each tester is separately annealed to excess driver in the first annealing and then pooled and again annealed in the second annealing to excess driver. During the first annealing, sequences common to both populations anneal. Additionally the concentration of high and low abundance messages are normalized since annealing is faster for abundant molecules due to the second order kinetics of hybridization. During the second annealing cDNAs unique or overabundant to the tester can anneal together. Such molecules have different adapters at their ends. The addition of additional driver during the second annealing enhances the enrichment of the desired differentially expressed sequences. During subsequent PCR, molecules that have different adapters at each end amplify exponentially. Molecules which have identical adapters, or adapters at only one end, or no adapters (driver sequences) either do not amplify or undergo linear amplification. The end result is enrichment for cDNAs corresponding to differentially expressed messages unique to the tester or up regulated in the tester.

This technique was used to identify transcripts unique to cancer tissues or messages overexpressed in the cancer process. To do this, pairs of samples isolated from a cancer tissue were used as the "tester", and non-cancer tissue as the "driver". The non-cancer "driver" can be from the same individual and tissue as the tumor (Matched). Alternatively, the "driver" can be from a different individual but the same tissue as the tumor sample (unmatched). In some cases, the "driver" comprises mixtures of cDNAs derived from non-cancer tissues different from the cancer tissue. This approach allows the identification of transcripts whose expression is specific or up-regulated in the cancer tissue. Such transcripts may or may not be cancer specific in their expression.

Subtractive hybridization was carried out using as "tester" a mixture of three RNAs from human adenocarcinomas and as "driver" a mixture of RNAs from five human normal tissues (spleen, pancreas, heart, kidney and small intestine).

The subtracted mixture was cloned and two hundred clones were sequenced. One of the sequences matched Incyte clone ID 3966820. The electronic Northern for this clone showed the highest number of ESTs came from prostate, compared with other tissues (prostate 107 followed by uterus with 20).

The PCR-select clone detected a transcript of 1.9 kb by hybridization in Northern blots. Amongst 17 tissues tested prostate showed the highest abundance for this transcript.

Example 2

Relative Quantitation of Gene Expression

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene were evaluated for every sample in normal tissues, cancer tissues, and from cancers and the corresponding matched adjacent tissues. Subsequently, first strand cDNA was prepared with reverse transcriptase and the polymerase chain reaction was done using primers and Taqman probes specific to each target gene. The results were analyzed using the ABI PRISM 7700 Sequence Detector. The absolute numbers are relative levels of expression of the target gene in a particular tissue compared to the calibrator tissue.

Real-Time quantitative PCR was done using the following primers:

```
pro108 Reverse
GCCTTCAGCCGTGGGTAGT           (SEQ ID NO: 3)

pro108 Forward
GACAGCGGCTTCACCTTCTC          (SEQ ID NO: 4)
```

The absolute numbers depicted in Table 1 are relative levels of expression of the CSG referred to herein as pro108 (SEQ ID NO:1) in 11 normal different tissues. All the values are compared to normal pancreas (calibrator). These RNA samples are commercially available pools, originated by pooling samples of a particular tissue from different individuals.

TABLE 1

Relative Levels of CSG Pro108 Expression in Pooled Samples

| Tissue | NORMAL |
|---|---|
| Colon Ascending | 4.56 |
| Kidney | 0.78 |
| Liver | 5.66 |
| Ovary | 41.07 |
| Small Intestine | 0.78 |
| Spleen | 3.29 |
| Stomach | 11.39 |
| Testis | 2.04 |
| Uterus | 15.56 |
| Pancreas | 1.00 |
| Prostate | 2.32 |

The relative levels of expression in Table 1 show the highest mRNA expression in ovary (41.07) and uterus (15.56), two female specific tissues. Except for stomach (11.39) that shows high levels of mRNA for pro108, the other tissues including prostate show comparable low levels of expression.

The absolute numbers in Table 1 were obtained analyzing pools of samples of a particular tissue from different individuals. They can not be compared to the absolute numbers originated from RNA obtained from tissue samples of a single individual in Table 2.

The absolute numbers depicted in Table 2 are relative levels of expression of the CSG pro108 in 70 pairs of matching samples. All the values are compared to normal pancreas (calibrator). A matching pair is formed by mRNA from the cancer sample for a particular tissue and mRNA from the normal adjacent sample for that same tissue from the same individual. Unmatched samples were used for prostatitis (prostatitis 1 and 2) and Benign Prostate Hyperplasia (BPH 1 to 6).

TABLE 2

Relative Levels of CSG Pro108 Expression in Individual Samples

| Sample ID | Tissue | Cancer | Benign Diseases | Normal Adjacent Tissue |
|---|---|---|---|---|
| Pro12B | Prostate 1 | 253.40 | | 7.70 |
| Pro78XB | Prostate 2 | 1020.46 | | 96.67 |
| Pro84XB | Prostate 3 | 2055.11 | | 70.52 |

TABLE 2-continued

Relative Levels of CSG Pro108 Expression in Individual Samples

| Sample ID | Tissue | Cancer | Benign Diseases | Normal Adjacent Tissue |
|---|---|---|---|---|
| Pro101XB | Prostate 4 | 872.61 | | 218.58 |
| Pro91X | Prostate 5 | 539.32 | | 195.36 |
| Pro13XB | Prostate 6 | 0.60 | | 0.49 |
| Pro23B | Prostate 7 | 929.30 | | 747.00 |
| Pro90XB | Prostate 8 | 160.50 | | 21.00 |
| Pro18XB | Prostate 9 | 45.63 | | 31.49 |
| Pro20XB | Prostate 10 | 312.50 | | 20.00 |
| Pro34B | Prostate 11 | 1351.18 | | 142.02 |
| Pro65XB | Prostate 12 | 1305.15 | | 8.37 |
| Pro69XB | Prostate 13 | 486.50 | | 14.50 |
| Pro10R | Prostatitis 1 | | 122.45 | |
| Pro20R | Prostatitis 2 | | 83.38 | |
| Pro258BPH | BPH 1 | | 39.33 | |
| Pro263CBPH | BPH 2 | | 451.98 | |
| Pro267ABPH | BPH 3 | | 90.78 | |
| Pro271ABPH | BPH 4 | | 5.21 | |
| Pro460ZBPH | BPH 5 | | 15.64 | |
| ProC032BPH | BPH 6 | | 46.85 | |
| Bld32XK | Bladder 1 | 2.86 | | 3.88 |
| Bld46XK | Bladder 2 | 15.62 | | 1.45 |
| Bld66X | Bladder 3 | 32.67 | | 19.90 |
| BldTR14 | Bladder 4 | 330.60 | | 235.50 |
| ClnAS67 | Colon 1 | 71.26 | | 0.51 |
| ClnRC01 | Colon 2 | 5.08 | | 25.90 |
| ClnSG45 | Colon 3 | 19.09 | | 6.61 |
| ClnSG67 | Colon 4 | 65.12 | | 20.61 |
| ClnTX01 | Colon 5 | 116.97 | | 6.25 |
| ClnB34 | Colon 6 | 3.98 | | 2.45 |
| ClnB56 | Colon 7 | 1.98 | | 1.41 |
| ClnC9XR | Colon 8 | 6.88 | | 2.00 |
| ClnCXGA | Colon 9 | 2.25 | | 2.62 |
| ClnAS89 | Colon 10 | 77.44 | | 2.39 |
| ClnTX67 | Colon 11 | 167.73 | | 11.51 |
| End10479 | Endometrium 1 | 7.63 | | 26.67 |
| End8911 | Endometrium 2 | 16.19 | | 64.98 |
| End8963 | Endometrium 3 | 12.14 | | 65.89 |
| End5XA | Endometrium 4 | 99.39 | | 23.51 |
| End65RA | Endometrium 5 | 6.94 | | 16.06 |
| Kid109XD | Kidney 1 | 65.57 | | 41.93 |
| Kid10XD | Kidney 2 | 39.67 | | 9.71 |
| Kid11XD | Kidney 3 | 12.68 | | 1.62 |
| Kid126XD | Kidney 4 | 43.71 | | 7.59 |
| Kid12XD | Kidney 5 | 2.50 | | 70.80 |
| Kid5XD | Kidney 6 | 2.11 | | 74.29 |
| Kid6XD | Kidney 7 | 19.36 | | 0.72 |
| Liv42X | Liver 1 | 39.00 | | 6.40 |
| Liv15XA | Liver 2 | 9.23 | | 4.59 |
| Liv94XA | Liver 3 | 7.07 | | 8.09 |
| LngAC66 | Lung 1 | 47.30 | | 16.20 |
| LngBR94 | Lung 2 | 106.50 | | 3.40 |
| LngLC109 | Lung 3 | 9.60 | | 34.10 |
| LngLC71 | Lung 4 | 70.30 | | 64.00 |
| LngSQ56 | Lung 5 | 12.40 | | 53.80 |
| LngSQ79 | Lung 6 | 108.40 | | 77.20 |
| Lng60XL | Lung 7 | 0.55 | | 1.47 |
| Lng75XC | Lung 8 | 2.34 | | 3.11 |
| LngC17X | Lung 9 | 52.96 | | 31.71 |
| LngAC69 | Lung 10 | 654.84 | | 42.67 |
| LngC20X | Lung 11 | 2.82 | | 0.22 |
| Mam47XP | Mammary Gland 1 | 3.40 | | 1.89 |
| Mam82XI | Mammary Gland 2 | 33.29 | | 4.44 |
| MamB011X | Mammary Gland 3 | 10.61 | | 1.50 |
| MamA06X | Mammary Gland 4 | 14.62 | | 1.55 |
| Ovr | Ovary | 10.00 | | 8.00 |
| Pan77X | Pancreas 1 | 91.27 | | 24.50 |
| Pan71XL | Pancreas 2 | 1.55 | | 1.30 |
| Pan82XP | Pancreas 3 | 5.49 | | 7.53 |
| Pan92X | Pancreas 4 | 1069.00 | | 688.40 |
| StoAC99 | Stomach 1 | 50.70 | | 18.60 |
| StoTA73 | Stomach 2 | 37.70 | | 130.30 |
| SmI21XA | Small Intestine 1 | 12.42 | | 5.31 |
| SmIH89 | Small Intestine 2 | 23.26 | | 2.63 |
| Tst39X | Testis | 27.95 | | 7.01 |
| Utr85XU | Uterus 1 | 3.30 | | 4.91 |
| Utr23XU | Uterus 2 | 44.48 | | 29.04 |

Table 2 shows the results for the analysis of 148 samples distributed in 14 different tissue types. Tables 1 and 2 represent a combined total of 159 samples in 16 different tissue types.

In the analysis of matching samples, the higher levels of expression were in prostate, showing a high degree of tissue specificity for prostate tissue. Of all the samples different from prostate which were analyzed (57 matching samples), only a few samples (lung 10 and pancreas 4) showed an expression comparable or higher than the median for the mRNA expression in prostate cancer (median: 539.32).

In addition, the level of mRNA expression in cancer samples was compared with the isogenic normal adjacent tissue from the same individual. This comparison provides an indication of specificity for the cancer stage (e.g. higher levels of mRNA expression in the cancer sample compared to the normal adjacent). Table 2 shows overexpression of the CSG pro108 in 13 of 13 prostate cancer tissues compared with their respective normal adjacent (prostate samples #1 to #13). Thus, there was overexpression in the cancer tissue for 100% of the prostate matching samples tested.

Altogether, the level of tissue specificity, plus the mRNA overexpression in 100% of the prostate matching samples tested are indicative of the CSG pro108 being a diagnostic marker for prostate cancer.

What is claimed is:

1. A method for diagnosing the presence of cancer in a patient comprising:
   (a) measuring levels of CSG in cells, tissues or bodily fluids from a patient; and
   (b) comparing the measured levels of CSG with levels of CSG in a noncancerous control, wherein an increase of 2 times higher in measured levels of CSG from said patient versus said control is associated with the presence of cancer,
   wherein said CSG comprises SEQ ID NO:2.

2. A method of imaging cancer in a patient comprising administering to the patient an antibody which specifically binds CSG comprising SEQ ID NO:2.

3. The method of claim 2 wherein said antibody is labeled with paramagnetic ions or a radioisotope.

* * * * *